United States Patent [19]
Asakura et al.

[11] Patent Number: 5,916,785
[45] Date of Patent: Jun. 29, 1999

[54] PROCESS OF OXIDIZING ALCOHOLS OR CARBOXYLIC ACIDS WITH ALCOHOL/ ALDEHYDE DEHYDROGENASE FROM GLUCONOBACTER

[75] Inventors: Akira Asakura; Tatsuo Hoshino, both of Kanagawa-ken, Japan

[73] Assignee: Roche Vitamins Inc., Parsippany, N.J.

[21] Appl. No.: 08/880,176

[22] Filed: Jun. 20, 1997

Related U.S. Application Data

[60] Continuation of application No. 08/405,483, Mar. 16, 1995, abandoned, which is a division of application No. 08/162,736, Dec. 3, 1993, Pat. No. 5,437,989.

[30] Foreign Application Priority Data

Dec. 30, 1992 [EP] European Pat. Off. .............. 92811029

[51] Int. Cl.⁶ ................................ C12P 7/26; C12P 7/02
[52] U.S. Cl. .......................... 435/148; 435/155; 435/138; 435/136; 435/147; 435/190
[58] Field of Search ................... 435/138, 148, 435/136, 155, 147, 190

[56] References Cited

U.S. PATENT DOCUMENTS

| | | |
|---|---|---|
| 3,922,194 | 11/1975 | Sonoyama . |
| 3,998,697 | 12/1976 | Sonoyama . |
| 4,352,885 | 10/1982 | Zukus . |
| 4,916,069 | 4/1990 | Fujiwara . |
| 4,935,359 | 6/1990 | Yin . |
| 4,960,695 | 10/1990 | Hoshino . |
| 5,082,785 | 1/1992 | Manning . |
| 5,250,428 | 10/1993 | Hoshino . |
| 5,312,741 | 5/1994 | Hoshino . |
| 5,352,599 | 10/1994 | Fujiwara . |
| 5,541,108 | 7/1996 | Fujiwara . |

FOREIGN PATENT DOCUMENTS

| | | |
|---|---|---|
| 0 098 136 | 1/1984 | European Pat. Off. . |
| 0 248 400 | 12/1987 | European Pat. Off. . |
| 0 248 401 | 12/1987 | European Pat. Off. . |
| 0 278 447 | 8/1988 | European Pat. Off. . |
| 0 366 922 | 5/1990 | European Pat. Off. . |
| 0 518 136 | 12/1992 | European Pat. Off. . |
| 3012278 | 1/1988 | Japan . |
| 3012279 | 1/1988 | Japan . |
| WO 89/06688 | 7/1989 | WIPO . |

OTHER PUBLICATIONS

Ghosh, et al, J. Biochem, vol. 199, pp. 245–250 (1981).
Groen, et al. J. Biochem, vol. 223, pp. 921–924 (1984).
Groen et al, J. Biochem, vol. 234, pp. 611–615 (1986).
Anthony, Advances in Microbial Phys. vol. 27, pp. 113–209 (1986).
Adachi, et al, Purification and Characterization of Particulate Alcohol Dehydrogenase from Gluconobacter suboxydans, Agric. Biol. Chem. 42(11), pp. 2045–2056 (1978).
Kitamura, et al, Metabolism of L–Sorbose by Enzymes from Gluconobacter melangenus IFO 3293, Europ. J. Applied Microbiology, vol. 2, pp. 1–8 (1975).
Sato, et al, Enzymatic Studies on the Oxidation of Sugar and Sugar Alcohol, The Journal of Biochemistry, vol. 66, No. 4, pp. 521–527 (1969).

*Primary Examiner*—Irene Marx
*Attorney, Agent, or Firm*—George W. Johnston; Dennis P. Tramaloni; Eileen M. Ebel

[57] ABSTRACT

The present invention relates to a novel alcohol/aldehyde dehydro-genase (hereinafter referred to as AADH), a process for producing the same and a process for producing aldehydes, carboxylic acids and ketones, especially 2-keto-L-gulonic acid (hereinafter referred to as 2-KGA) utilizing said enzyme.

8 Claims, No Drawings

PROCESS OF OXIDIZING ALCOHOLS OR CARBOXYLIC ACIDS WITH ALCOHOL/ ALDEHYDE DEHYDROGENASE FROM GLUCONOBACTER

This is a continuation of application Ser. No. 08/405,483 filed Mar. 16, 1995, now abandoned, which is a divisional of U.S. Ser. No. 08/162,736, filed Dec. 3, 1993, now U.S. Pat. No. 5,437,989.

BACKGROUND OF THE INVENTION

It is known that there are enzymes which catalyze the oxidation of alcohols and aldehydes to aldehydes and carboxylic acids, respectively, and have pyrroloquinoline quinone ("PQQ") as a prosthetic group.

Methanol dehydrogenases, which are members of alcohol dehydro-genases, catalyze not only the oxidation of methanol to aldehyde, but also formaldehyde to formic acid and formate (Advances in Microbial Physiology, 27, 113–209, 1986). These methanol dehydrogenases oxidize a wide range of primary alcohols, such as methanol and ethanol and some aldehydes but most of these enzymes cannot oxidize secondary alcohols. The methanol dehydrogenases derived from Methylobacterium organophilum, Pseudomonas C, Diplococcus PAR, and Rhodopseudomonas acidophile are examples of dehydrogenases which can catalyze the oxidation of secondary alcohols. To carry out the oxidation of alcohols and aldehydes, the methanol dehydrogenases use activators, such as methylamine or ammonia.

Quinoprotein alcohol dehydrogenase from Pseudomonas aeruginosa (Biochem. J., 223, 921–924, 1984) and quino-haemprotein alcohol dehydrogenase from Pseudomonas testosteroni (Biochem., J., 234, 611–615, 1986) are other examples of alcohol dehydrogenases having PQQ as a prosthetic group. The former enzyme is a monomer whose molecular weight is 101,000 and requires ammonium salts or amines as activators. The latter enzyme is a monomer, whose molecular weight is about 67,000, and contains one haem c group in its molecule.

SUMMARY OF THE INVENTION

The present invention relates to a novel alcohol/aldehyde dehydro-genase ("AADH"), a process for producing the same and a process for producing aldehydes, carboxylic acids and ketones, especially 2-keto-L-gulconic acid ("2-KGA") utilizing said enzyme.

The AADH provided by the present invention catalyzes the oxidation of alcohols and aldehydes, and is thus capable of producing the corresponding oxo group from alcohols, and carboxylic acids from aldehydes. More particularly, the AADH provided by the present invention catalyzes the oxidation of L-sorbose to 2-KGA via L-sorbosone. 2-KGA is an important intermediate for the production of vitamin C.

DETAILED DESCRIPTION OF THE INVENTION

The AADH provided by the present invention oxidizes a wide range of primary and secondary alcohols to form a corresponding oxo group, and oxidizes aldehydes to form carboxylic acids. The AADH provided by the present invention catalyzes the oxidation of L-sorbose to 2-KGA via L-sorbosone. 2-KGA is an important intermediate for the production of vitamin C. As used throughout this specification the term oxo group refers to aldehydes and ketones. The corresponding oxo group from a primary alcohol is an aldehyde. The corresponding oxo group from a secondary alcohol is a ketone.

There have been no reports up to now concerning an AADH as provided by the present invention. The novel AADH reported herein is clearly distinct from the previously mentioned methanol dehydrogenases in the following ways: AADH hardly oxidizes methanol, while ethanol is a good substrate; AADH does not require ammonia or methylamine as an activator and AADH has an isoelectric point about 4.4 while the isoelectric point of most methanol dehydrogenases is higher than 7.0.

The novel AADH is also distinct from the quinoprotein alcohol dehydrogenase mentioned above, in that, this AADH is not a monomer, but consists of two subunits and this AADH does not require the use of any activator. This AADH also differs from quinohaemprotein alcohol dehydrogenase, because this AADH is not a monomer and does not contain a haem c group.

The invention reported herein is a homogenous protein AADH produced by a microorganism of the genus Gluconobacter. This AADH is an active enzyme capable of oxidizing an alcohol to the corresponding oxo group, and oxidizing an aldehyde to a carboxylic group, in the presence of an electron acceptor. This AADH has a molecular weight of 135,000±5,000 daltons, and is composed of an alpha and beta subunit and a pyrroloquinoline quinone prosthetic group. The alpha subunit has a molecular weight of 64,500±2,000 daltons. The beta subunit has a molecular weight of 62,500±2,000 daltons.

The physio-chemical properties of the purified sample of AADH prepared by Examples mentioned herein are further described as follows:

1) Enzyme activity

The AADH of the present invention catalyzes the oxidation of alcohols and aldehydes, and is capable of producing aldehydes and ketones from alcohols, and carboxylic acids from aldehydes in the presence of an electron acceptor.

This electron acceptor may be any conventional compound which has the ability to act as an electron acceptor, such as 2,6-dichlorophenolindophenol, ("DCIP"), phenazine methosulphate ("PMS"), Wurster's blue, ferricyanide, coenzyme Q or cytochrome c. However, AADH does not utilize oxygen as an electron acceptor.

The enzyme assay was performed at 25° C. by measuring the decrease of absorbance at 600 nm of DCIP with a spectrophotometer (UVIKON 810, Kontron K.K.). One unit of the enzyme activity was defined as the amount of the enzyme which catalyzed the reduction of 1 $\mu$mole of DCIP per minute. The extinction coefficient of DCIP at pH 8.0 was taken as 15 mMol$^{-1}$. The standard reaction mixture (1.0 ml) contained 0.1 mMol DCIP, 1 mMol PMS, 125 mMol L-sorbose, 50 mMol Tris-malate-NaOH buffer (pH 8.0), and 3–8 $\mu$l of the enzyme solution. A reference cuvette contained all the above components except the substrate.

2) Substrate specificity

The substrate specificity of AADH was determined using the same enzyme assay method as described under section 1) above, except that various further substrates were used instead of L-sorbose. A variety of compounds such as primary alcohols, secondary alcohols, aldehydes and high molecular weight alcohols, such as polyethylene glycols or polyvinyl alcohols, can be the substrates for AADH.

3) Optimum pH

The correlation between the reaction rate of AADH and pH was determined in Tris-malate-NaOH buffer (pH 6.0 to 8.5) and in Tris-HCl buffer (pH 9.0) using a variety of substrates. Regardless of the kind of the substrates, AADH showed the highest activity at a pH range between 7.0 and 9.0. The optimum pH for enzyme activity is 7.0 to 9.0.

4) pH stability

Purified AADH was kept standing in buffers of various pH-values for a certain period at 4° C. The residual activity was assayed under the standard assay condition as described above under section 1) above using L-sorbose and L-sorbosone as the substrates. The results of the measurements are shown in Table 3. The purified enzyme was relatively stable in alkaline pH's and became unstable with increased acidity.

5) Heat stability

Purified AADH was treated for 10 minutes at various temperatures in 25 mMol Tris-HCl buffer (pH 8.0) containing 0.1 Mol NaCl and 5% sucrose, and then cooled immediately in ice water. The residual activity was measured under the standard assay conditions as described under section 1) above using a variety of substrates. AADH is rather stable at and below 30° C., while unstable above 40° C.

6) Optimum Temperature

The enzymatic activities of AADH were measured at temperatures from 10° C. to 50° C. in the reaction system as described under section 1) above using a variety of substrates. This enzyme showed its optimum activity at temperatures between 20° C. and 40° C.

7) Molecular Weight

The molecular weight of purified AADH was determined by gel filtration column chromatography. The sample was applied on a resin for the purification of proteins, e.g. Sephacryl S-300HR (Pharmacia) column equilibrated with 25 mMol Tris-HCl buffer (pH 8.0) containing 0.1 Mol NaCl and 5% sucrose. As molecular weight standards, thyroglobulin (670,000 dalton), ferritin (450,000 dalton), catalase (240,000 dalton), aldolase (158,000 dalton), gamma globulin (158,000 dalton), bovine serum albumin (66,200 dalton), ovalbumin (45,000 dalton), chymotrypsinogen A (25,000 dalton), myoglobin (17,000 dalton), cytochome c (12,500 dalton) and vitamin $B_{12}$ (1,359 dalton) were used. As a result, the molecular weight of AADH was determined to be 135,000±5,000 dalton. Next, purified AADH was treated by sodium dodecyl sulfate (SDS) in the presence of beta-mercaptoethanol and analyzed for its molecular structure by SDS-polyacrylamide gel electrophoresis. As molecular weight standards, phosphorylase B (92,500 dalton), bovine serum albumin (66,200 dalton), ovalbumin (45,000 dalton), carbonic anhydrase (31,000 dalton), soybean trypsin inhibitor (21,500 dalton) and lysozyme (14,400 dalton) were used. It was shown that the enzyme AADH consists of two subunits. One (alpha subunit) has a molecular weight of 64,500±2,000 dalton and the other (beta subunit) has a molecular weight of 62,500±2,000 dalton.

8) Measurement of the Km (Michaelis constant) values

In the procedure described under section 1), the velocities of oxidizing reactions with varying concentrations of several substrates were measured to determine the apparent Michaelis constant (Km). The mixture of DCIP and PMS was used as electron acceptors. The Km values for L-sorbose and 1-propanol were calculated to be 230 mMol and 2 mMol, respectively.

9) Effect of metal ions

Using the assay procedure described under section 1), the effect of various metal ions on the enzyme activity was examined. Among the ions tested, only $Mg^{2+}$ and $Ca^{2+}$ did not affect the AADH activity. The others affected the enzyme activity strongly or moderately. $Cu^{2+}$, $Mn^{2+}$ and $Fe^{3+}$ are strong inhibitors for the enzyme.

10) Effect of inhibitors

Using the assay procedure described under section 1) above, the effect of inhibitors on the enzyme activity was examined. Ethylenediamine tetraacetic acid ("EDTA") and ethylene glycol bis(beta-aminoethylether)-N,N,N',N'-tetraacetic acid ("EGTA") strongly inhibited the enzyme activity.

11) Prosthetic group

The absorption spectrum of purified AADH showed an absorption maximum at 280 nm followed by a shoulder at 290 nm. The second peak was detected at 340 nm with a wide shoulder at 380–420 nm. This absorption spectrum strongly suggested that AADH has PQQ as a prosthetic group.

Purified AADH (4.5 mg) in 100 mMol $NaH_2PO_4$-HCl (pH about 1.0) was added to an equal volume of methanol and mixed. The sample was then centrifuged at 15,000 rpm for 10 minutes to remove the precipitate. The resulting extract was used for the analysis of the prosthetic group. The absorption spectrum of the extract was completely identical with an authentic sample of PQQ (Mitsubishi Gas Chemical Co.). Furthermore, by high pressure liquid chromatography analysis, using a reverse phase column (TSK-ODS 80 TM, Toyo Soda CO.), the extract from AADH showed the same retention time as that of authentic PQQ.

12) Isoelectric point

The isoelectric point (pI) of AADH was determined. Polyacrylamide gel (4%) containing 8.5 Mol urea, 2% (w/v) a non-ionic detergent, e.g. Nonidet P-40 and 2.4% (w/v) of an Ampholite, a buffer component for the pH-gradient, namely Pharmalyte, pH 2.5–5.0 (Pharmacia), was used for isoelectric focusing. The electrode solutions were 0.01 Mol iminodiacetate for the anode and 0.01 M N-2-hydroxyethylpiperazine-N'-2-ethanesulfonic acid (HEPES) buffer for the cathode. The isoelectric point of the sample was estimated in comparison with a low pH calibration kit, pH 2.5–5.0, purchased from Pharmacia. As a result, AADH showed a cluster containing a few bands having pI points at about 4.4.

13) Purification method

The purification of AADH may, in principle, be effected by any combination of known purification methods, such as:

fractionation with precipitants, e.g. ammonium sulfate, polyethylene glycol, etc.

ion exchange chromatography, adsorption chromatography, gel-filtration chromatography, gel electrophoresis, salting out and dialysis.

The AADH provided by the present invention can be prepared by cultivating an appropriate microorganism, disrupting the cells and isolating and purifying it from cell free extract of disrupted cells, preferably from the cytosol fraction of the microorganism.

The microorganisms used in the present invention includes all strains belonging to the genus Gluconobacter which are capable of producing AADH characterized hereinbefore. Functional equivalents, subcultures, mutants and variants of said microorganism that are also capable of producing AADH characterized above can be also used in the present invention. To determine whether a microorganism of the genus Gluconobacter, or any functional equivalent, subculture, mutant or variant thereof, is capable of producing the novel AADH characterized above, the microorganism can first be cultured under aerobic conditions in nutrient medium described herein, then the AADH may be isolated and purified by conventional means, and the above-listed thirteen (13) physio-chemical properties of the purified sample of AADH can be determined and compared to the AADH characterized above.

A preferred strain is a specific Gluconobacter oxydans strain, which has been deposited at the Deutsche Sammlung von Mikroorganismen in Göbttingen (Germany) under DSM No. 4025 on Mar. 17, 1987. (The present address of this institute is Deutsche Sammlung Von Mikroorganismen und ZellKulturen GmbH, Mascheroder Weg 1b, D-3300 Braunschweig, Germany).

Moreover, a subculture of said strain has also been deposited in the Agency of Industrial Science and Technology, Fermentation Research Institute, Japan, under the stipulations of the Budapest Treaty under the deposit No.:

Gluconobacter oxydans DSM No. 4025 FERM BP-3812 (date of deposit: Mar. 30, 1992). (The present address of this institute is National Institute of Bioscience and Human Technology, Agency of Industrial Science and Technology, Ministry of International Trade and Industry, 1–3, Higashi 1-chome, Tsukuba-shi, Ibaraki-ken 305, Japan).

Furthermore, European Patent Publication No. 0278 447 (4226/081k) discloses the characteristics of this preferred strain of Gluconobacter oxydans. Any microorganism having the identifying characteristics of Gluconobacter oxydans DSM No. 4025 (FERM BP-3812) may be used in the present invention as a source of novel AADH having the thirteen (13) physio-chemical properties described above. One may determine whether a microorganism has the identifying characteristics of the deposited strain of Gluconobacter DSM No. 4025 (FERM BP-3812), either by assay or by direct comparison with the deposited strain.

The microorganisms may be cultured in an aqueous medium supplemented with appropriate nutrients under aerobic conditions. The cultivation may be conducted at pH's between about 4.0 and 9.0, preferably between about 6.0 and 8.0. While the cultivation period varies depending upon pH, temperature and nutrient medium used, usually 2 to 5 days will bring about favorable results. A preferred temperature range for carrying out the cultivation is from about 13° to 36° C., preferably from about 18° to 33° C.

It is usually required that the culture medium contains such nutrients as assimilable carbon sources, digestable nitrogen sources and inorganic substances, vitamins, trace elements and other growth promoting factors. As assimilable carbon sources, L-sorbose, glycerol, D-glucose, D-mannitol, D-fructose, D-arabitol and the like can be used.

Various organic or inorganic substances may also be used as nitrogen source. Among the preferred organic sources, meat extract, peptone, casein, corn steep liquor, urea, amino acids, nitrates, ammonium salts and the like can be enumerated. As examples of preferred inorganic substances, magnesium sulfate, potassium phosphate, ferrous and ferric chlorides, calcium carbonate and the like may be used.

In the following, an embodiment for the isolation and purification of AADH from microorganisms after the cultivation of these microorganisms is briefly described.

(1) Microorganism cells are harvested from the fermentation broth by centrifugation or filtration.
(2) These cells are suspended in a buffer solution and disrupted by means of a homogenizer, sonicator or treatment with lysozyme and the like to give a disrupted solution of cells.
(3) AADH is isolated and purified from a cell free extract of these disrupted cells, preferably from the cytosol fraction of the microorganisms.

The AADH provided by the present invention is useful as a catalyst for converting alcohols to corresponding oxo groups, such as aldehydes and ketones, and for converting aldehydes to carboxylic acids. This reaction wherein alcohols and aldehydes are oxidized, comprises the step of treating the alcohol or aldehyde by contact with the AADH enzyme described herein. This AADH enzyme is provided in either or homogenous form or in a non-homogenous form. When the alcohol aldehyde is treated by contact with a microorganism of the genus Gluconobacter, capable of producing the AADH described herein, or by contact with a cell-free extract of such microorganism, then the AADH is provided in a non-homogenous form. This AADH is especially useful for the production of 2-KGA from L-sorbose via L-sorbosone.

These reactions utilizing AADH as a catalyst should be conducted at pH values from about 6.0 to about 9.0 in a solvent in the presence of an electron acceptor. Examples of electron acceptors that may be used include DCIP, PMS, Wurster's blue, ferricyanide, coenzyme Q, cytochrome c and the like. Any conventional solvent may be used. The preferred solvents include Tris-HCl buffer, phosphate buffer and the like.

The reaction temperature is not critical; however, the preferred temperature range for carrying out the above reaction is from about 10° C. to about 50° C. When the reaction is carried out at pH from 7.0–8.0 and a temperature within the range of 20° C. and 40° C., best results are obtained.

The concentration of the substrate in a solvent can vary depending on other reaction conditions. A substrate concentration from about 10 g/l to about 100 g/l is preferable. Best results are obtained when the concentration of the substrate is from about 30 g/l to about 40 g/l.

In the above reaction, AADH may also be used in an immobilized state with an appropriate carrier. Any means of immobilizing enzymes generally known to the art may be used. For instance, the enzyme may be bound directly to a membrane, or a resin. When AADH is bound to a resin, the enzyme may be bound directly to resin granules by functional group(s), or the enzyme may be bound to the resin indirectly through bridging compounds which have functional group(s). The preferred bridging compound is glutaraldehyde.

In addition to the above, the cultures cells are also useful for the production of aldehydes and ketones from alcohols and for the production of carboxylic acids from aldehydes, especially for the production of 2-KGA from L-sorbose via L-sorborsone.

The following examples further illustrate the present invention.

EXAMPLE 1

Preparation of AADH

All the operations were performed at 4° C. unless otherwise described.

(1) Cultivation of Gluconobacter oxydans DSM No. 4025 (FERM BP-3812)

(a) Preparation of the medium

A seed culture medium containing L-sorbose 8% (w/v) (separately sterilized), glycerol 0.05% $MgSO_4.7H_2O$ 0.25%, corn steep liquor 1.75%, baker's yeast 5.0%, $CaCO_3$ 0.5% and urea 0.5% (separately sterilized) (pH 7.0 before sterilization) was put into a test tube (5 ml each) and sterilized at 120° C. for 20 minutes.

(b) Inoculation, Incubation

Into this seed culture medium, one loopful of the cells of Gluconobacter oxydans DSM No. 4025 (FERM BP-3812) grown on a slant culture medium containing D-mannitol 5.0% in warter, $MgSO_4 \cdot 7H_2O$ 2.5%, corn steep liquor 1.75%, baker's yeast 0.25%, $CaCO_3$ 0.5%, urea 0.5% (separately sterilized) and agar 2.0%, (pH 7.0 before sterilization) at 27° C. for four days was inoculated and incubated at 30° C. for 24 hours. The resulting seed culture (5 ml) was inoculated into 100 ml of the same seed culture medium as described above in a 500 ml-Erlenmeyer flask and incubated at 30° C. for 24 hours. Further, the resulting seed culture (5 ml) was inoculated into 100 ml of the same seed culture medium as described above in a 500 ml-Erlenmeyer flask and incubated at 30° C. for 24 hours. 750 ml of the seed culture thus prepared were used for the inoculation of 15 l of a main medium in a 30 l jar fermentor. The medium contained L-sorbose 10.0% (sterilized separately), glycerol 0.05%, urea 1.6% (sterilized separately), $MgSO_4 \cdot 7H_2O$ 0.25%, baker's yeast 5.0%, CaCO3 1.5% and corn steep liquor 3.0%. The fermentation was carried out at 30° C., 500 rpm for the agitation and 7.5 l/minute for the aeration. After 40 hours fermentation, the culture was harvested by centrifugation (10,000 g, 15 minutes). The cell cake was suspended in 1 l of 25 mMol Tris-HCl, pH 7.5, containing 0.9% NaCl, 5 mMol $MgCl_2$ and 1 mMol phenylmethylsulfanyl fluoride (PMSF). The suspension was centrifuged at 500 g for 5 minutes to precipitate down $CaCO_3$ and other precipitatable medium ingredients. Then, the cells were collected by centrifugation at 10,000 g for 15 minutes. The operation as mentioned above was repeated again. As a result, 125 g (wet weight) of the cells of Gluconobacter oxydans DSM No. 4025 (FERM BP-3812) were obtained. The washed cells were frozen at −20° C. for one week before the next purification step.

(2) Preparation of the cytosol fraction

The cells of Gluconobacter oxydans DSM No. 4025 (FERM BP-3812) (125 g) from the above step (1) were suspended in 100 ml of 25 mMol Tris-HCl buffer, pH 8.0, containing 0.5 mMol PMSF and subjected twice to a (French press) cell disrupter to break the cells (1,500 kg/cm²). Into this homogenized suspension, 2 ml of 1 mg/ml of the DNA splitting DNase I (Sigma) and 1 ml of 0.5 Mol $MgCl_2$ were added, the mixture kept standing for 15 minutes and centrifuged at 6,000 g for 15 minutes to remove the cell debris. The cell free extract (210 ml) thus obtained was centrifuged at 100,000 g for 60 minutes. The resulting supernatant was collected as the cytosol fraction (200 ml).

(3) PEG (MW 6000) treatment (precipitation of the DNA)

The cytosol fraction (200 ml) from step (2) was dialyzed overnight against 2 liters of 25 mMol Tris-HCl buffer, pH 8.0, containing 0.25 mMol PMSF; then 40 g of PEG 6000 (Nakarai Chemicals Ltd.) and 5 ml of 2 N KCl, were added and the mixture stirred for 30 minutes and centrifuged at 14,000 g for 20 minutes. The supernatant was filled up to 400 ml with the same buffer.

(4) DEAE Toyopearl 650 M (weak ion-exchange) column chromatography [first step]

The supernatant (400 ml) obtained from the above step (3) was applied to a diethylaminoethyl (DEAE) Toyopearl 650 M column (2.5 cm in diameter and 35 cm in length), which had been equilibrated with 25 mMol Tris-HCl buffer, pH 8.0, containing 0.25 mMol PMSF and 5% sucrose. After the column was washed with 600 ml of the same buffer, the enzyme was eluted by a linear gradient of NaCl from 0 to 0.5 Mol in the same buffer (2,000 ml). The active fractions were pooled (174 ml) and subjected to the next step.

(5) Q-Sepharose (strong-ion exchange) column chromatography [second step]

The active fractions in the previous step were applied to a Q-Sepharose column (2.5 cm in diameter and 35 cm in length) which had been equilibrated with 25 mMol Tris-HCl buffer, pH 8.0, containing 5% sucrose. After the column was washed with the buffer to the baseline, the elution of the enzyme was performed with a linear gradient of 0.25 to 0.5 Mol NaCl in the same buffer (2,000 ml). The fractions which contained electrophoretically homogenous AADH were combined and concentrated to 20 ml by ultrafiltration using a PM-30 (Amicon Corporation) membrane.

(6) Purity of isolated AADH

For the estimation of the purity of isolated AADH, a polyacrylamide gel electrophoresis was performed. The sample was applied to 7.5% polyacrylamide gel in Tris-HCl buffer, pH 9.4, according to the procedure of Davis et al. (Ann. N.Y. Acad. Sci. 121: 404, 1969). Proteins were stained with the protein colourant Coomassie Brilliant Blue R-250. The enzyme activity in the gel was detected by coupling it under the reduction of nitro blue tetrazolium chloride (Sigma). The gel was immersed at 30° C. in the dark in a solution containing 50 mMol Tris-malate buffer, pH 8.0, 0.01 mMol PQQ, 0.1 mMol PMS, 0.4 mMol nitroblue tetrazolium chloride and 0.25 Mol L-sorbose.

AADH showed the closely spaced three bands by protein staining, and all the bands had enzyme activity. The appearance of three protein bands on the gel is due to the dissociation of the prosthetic group, PQQ, from the enzyme during electrophoresis.

(7) Identification of reaction product

A reaction mixture containing 50 ml of the purified AADH (1.5 mg protein), 0.1 ml of 10 mMol PMS, 0.5 ml of 0.4 Mol sodium phosphate buffer, pH 6.5, 0.25 ml of water and 0.1 ml of 20% solution of the various substrates was incubated at 30° C. for 15 hours with gentle shaking. The reaction product was analyzed by thin layer chromatography. Products were identified by the direct comparison with authentic samples.

EXAMPLE 2

2-KGA production by purified AADH

A reaction mixture containing 0.5 ml of purified AADH (15 mg protein, and prepared according to Example 1), 1 ml of a 20% solution of L-sorbose, 1 ml of 10 mMol PMS, 5 ml of 0.4 M sodium phosphate buffer, pH 6.5 and 2.5 ml of water was incubated at 30° C. with gentle shaking. As a result, 2-KGA was formed with the rate of about 70 mg/hour.

EXAMPLE 3

2-KGA production under a resting cell system

The reaction mixture (10 ml): 0.25 g of the cells of Gluconobacter oxydans DSM No. 4025 (FERM BP-3812) prepared in the same manner as described in step (1) of Example 1, 1 ml of a 20% solution of L-sorbose, 1 ml of 10 mMol PMS, 1 ml of a 3% aqueous solution of NaCl, 1 ml of 30 mMol PQQ, 0.1 g of $CaCO_3$ and water, was incubated at 30° C. with gentle shaking. As a result, 2-KGA formation was observed with the rate of about 6 mg/hour.

We claim:

1. A process for converting an alcohol group to its corresponding oxo group, comprising treating the alcohol with a purified alcohol/aldehyde dehydrogenase Gluconobacter enzyme in the presence of an amount of an electron acceptor sufficient for catalysis to occur,
wherein the enzyme
- oxidizes an alcohol group to the corresponding oxo group in the presence of an amount of an electron acceptor sufficient for catalysis to occur;
- has a molecular weight from 130,000 daltons to 140,000 daltons as determined by gel filtration column chromatography;
- is comprised of an alpha subunit having a molecular weight from 62,500 daltons to 66,500 daltons, a beta subunit having a molecular weight from 60,500 daltons to 64,500 daltons, and a pyrroloquinoline quinone prosthetic group;
- has an optimum pH for dehydrogenase activity of from 7.0 to 9.0;
- has an optimum temperature for dehydrogenase activity from 20° C. to 40° C.;
- and has an isoelectric point of about 4.4 converting the alcohol to its corresponding oxo group, thereby converting the alcohol to its corresponding oxo group.

2. The process of claim 1, wherein the enzyme is purified from Gluconobacter oxydans.

3. The process of claim 1, wherein said process is carried out at a temperature from about 20° C. to about 40° C. and a pH from about 7.0 to about 8.0.

4. The process of claim 1, wherein said enzyme is a homogenous protein.

5. A process for producing a carboxylic acid from its corresponding aldehyde, comprising treating the aldehyde with a purified alcohol/aldehyde dehydrogenase Gluconobacter enzyme in the presence of an amount of an electron acceptor sufficient for catalysis to occur,
wherein the enzyme
- oxidizes an aldehyde to a carboxylic acid in the presence of an amount of an electron acceptor sufficient for catalysis to occur;
- has a molecular weight from 130,000 daltons to 140,000 daltons as determined by gel filtration column chromatography;
- is composed of an alpha subunit having a molecular weight from 62,500 daltons to 66,500 daltons, a beta subunit having a molecular weight from 60,500 daltons to 64,500 daltons, and a pyrroloquinoline quinone prosthetic group;
- has an optimum pH for dehydrogenase activity of from 7.0 to 9.0;
- has an optimum temperature for dehydrogenase activity from 20° C. to 40° C.;
- and has an isoelectric point of about 4.4 producing the carboxylic acid from the aldehyde, thereby producing the carboxylic acid from its corresponding aldehyde.

6. The process of claim 5, wherein the process is carried out at a temperature from about 20° C. to about 40° C. and a pH from about 7.0 to about 8.0.

7. The process of claim 5, wherein said enzyme is a homogenous protein.

8. The process of claim 5, wherein the enzyme is purified from Gluconobacter oxydans.

* * * * *